United States Patent
Hoehe et al.

(10) Patent No.: US 6,383,756 B1
(45) Date of Patent: May 7, 2002

(54) METHOD FOR NON-RADIOACTIVE DETECTION OF MEMBRANE-BONDED NUCLEIC ACIDS AND TEST KIT

(75) Inventors: Margret Hoehe; Sebastian Delbruck, both of Berlin (DE)

(73) Assignee: Genprofile AG, Berlin (DE)

( * ) Notice: Subject to any disclaimer, the term of this patent is extended or adjusted under 35 U.S.C. 154(b) by 0 days.

(21) Appl. No.: 09/674,708

(22) PCT Filed: May 3, 1999

(86) PCT No.: PCT/DE99/01066

§ 371 Date: Jan. 22, 2001

§ 102(e) Date: Jan. 22, 2001

(87) PCT Pub. No.: WO99/57307

PCT Pub. Date: Nov. 11, 1999

(30) Foreign Application Priority Data

May 6, 1998 (DE) .......................................... 198 21 116
Dec. 7, 1998 (DE) .......................................... 198 56 391

(51) Int. Cl.⁷ .................................................. C12Q 1/68
(52) U.S. Cl. ......................................................... 435/6
(58) Field of Search ............................................... 435/6

(56) References Cited

FOREIGN PATENT DOCUMENTS

EP        0303459  B1     2/1989

OTHER PUBLICATIONS

Bronstein et al., "Detection of DNA in Southern blots with Chemiluminescence", Meth. Enzymol. vol. 217, pp. 398–414 (1993).*

E. S. Lander, Science, vol. 274, pp. 536–539 (Oct. 25, 1996).

F. S. Collins et al., Science, vol. 278, pp. 1580–1581 (Nov. 28, 1997).

E. Marshall, Science, vol. 277, pp. 1752–1753 (Sep. 19, 1997).

P. Richterich et al., Methods in Enzymology, vol. 218, pp. 187–222 (1993).

* cited by examiner

*Primary Examiner*—Kenneth R. Horlick
*Assistant Examiner*—Teresa Strzelecka
(74) *Attorney, Agent, or Firm*—Birch, Stewart, Kolasch & Birch, LLP

(57) ABSTRACT

The present invention relates to a novel method for non-radioactive detection of membrane-bonded nucleic acids, including nucleic acids that, for instance, contain single nucleotide polymorpbisms (SNP's), DNA arrays (cosmide, yeast, artificial chromosones (YAC's), bacterial artificial chromosones (BAC's), cDNA's, PCR fragments, oligonucleotides), RNA arrays and all nucleic acid fragments that are tranfered from gels (agarose or PAA) to membranes, including genomic DNA/plasmid DNA fragments (southern) and mRNA's (northern). The invention also relates to a test kit to carry out said method.

7 Claims, No Drawings

METHOD FOR NON-RADIOACTIVE DETECTION OF MEMBRANE-BONDED NUCLEIC ACIDS AND TEST KIT

This application is the national phase under 35 U.S.C. § 371 of PCT International Application No. PCT/DE99/01066 which has an International filing date of May 3, 1999, which designated the United States of America.

DESCRIPTION

The present invention relates to a novel method for non-radioactive detection of membrane-bonded nucleic acids, including nucleic acids that, for instance, contain single nucleotide polymorphisms (SNPs), DNA arrays (cosmids, yeast artificial chromosomes (YAC's), bacterial artificial chromosomes (BAC's), cDNA's, PCR fragments, oligonucleotides), RNA arrays and all nucleic acid fragments that are transferred from gels (agarose or polyacrylamide (PAA) gels) to membranes, including genomic DNA/plasmid DNA fragments (Southern) and mRNAs (Northern) and a test kit to apply the method.

Arrays are individual nucleic acids preferably arranged to a defined degree on a membrane in rasters.

The identification of exchanges of individual bases within DNA (SNP's) is of great importance to investigating the causes of complex diseases, e. g. hypertension, and for diagnostic purposes (Lander, E. S. (1996): Science 274, 536–539, Collins, F. S. et al. (1997) Science 278, 1580–1581, Marshall E. (1997): Science 277, 1752–1753). Such an exchange is may be detected by sequencing the interesting regions.

Traditionally the sequence is determined by the enzymatic chain-terminating method where the sequencing products are marked by the incorporation of radioactively or non-radioactively labeled nucleotides. Following gel electrophoretic separation the sequence may be determined by evaluation of the sequence gels. Direct labelling of the sequencing products, however, has the disadvantage that only one single DNA fragment may be analyzed per sequencing batch.

Multiplex technology (see EP-A 0 303 459) overcomes this disadvantage by simultaneously sequencing a few DNA molecules. The resulting mixtures of sequencing products formed are gel electrophoretically separated, transferred to a nylon membrane and fixed there. By hybridizing this membrane with a probe which is specific for a single DNA fragment the sequences of a few DNA fragments may be successively read using the same membrane. However, a big disadvantage of this method is that the detection of various DNA fragments is effected by using radioactively labelled probes. That is why automation of the whole process to further increase the flow rate will not be feasible.

Furthermore, a non-radioactive detection method is known which is described by Richterich and Church (Richterich, R., Church, G. M (1993) Methods Enzymol 218: 187–222), however showing the disadvantages to be not suitable for successive hybridizations and usually hybridizations may not be carried out exclusively at room temperature.

The objective of the present invention is to establish an easy to perform non-radioactive method to be applied which maintains or even improves, on the one hand, the sensitivity of radioactive methods and, on the other hand, allows an immediate, direct successive detection.

The invention is implemented according to the claims. Surprisingly, this task may be solved by means of a method which may be applied in all stages at room temperature. The method according to the invention is suited for a non-radioactive detection of membrane-bound nucleic acids (A) by hybridizing NAs bound to a membrane which are obtained by means of methods known per se with a special hybridization buffer containing Tris HCl, Tris base, NaCl, Triton X-100, SDS and a blocking reagent and subsequently detecting the bound NA. The invention does not include the detection of sequencing products according to the multiplex method in accordance with EP 303 459 (G. Church).

Preferably membrane-bound DNA is detected.

The method is preferably characterized by the following steps:

1. Prehybridization of a membrane containing a DNA according to a method known per se, preferably in a dish, with the aid of a special hybridization buffer,
2. hybridization of the membrane by means of a 5'biotinylated probe in the same buffer,
3. repeated washing of the membrane with buffer I containing PBS ($Na_2HPO4$, $NaH_2PO_4$, NaCl, pH approx. 7.3), SDS and blocking reagent,
4. incubation of the membrane with streptavidin alkaline phosphatase conjugate in buffer I,
5. one-time washing of the membrane with buffer I, thereupon repeated washing with buffer II, containing PBS and SDS and repeated equilibration at pH 9.75 with buffer III containing Tris-HCl and diethanol amine,
6. after equilibration, transfer of the membrane into a substrate solution consisting of CDPstar® (disodium 2-chloro-5-(4-methoxyspiro{1,2-dioxetane-3,2'-(5-chloro)-tricyclo[$3.3.1.1^{3,7}$]decan}-4-yl)-1-phenyl phosphate, Tropix® and buffer III and, if necessary, agitation of the membrane to reach a uniform distribution of the substrate solution,
7. after short drainage, fixing of the membrane, e.g. onto a piece of plastic, and covering, preferably with a transparent foil,
8. exposing, preferably by means of an X-ray film or a CCD camera,
9. after exposure returning of the membrane and repeated stripping with a preheated buffer IV containing EDTA and SDS,
10. one-time washing with buffer V containing Tris-HCl and NaCl.

The evaluation is performed according to established methods such as e.g. the 'skilled pattern analysis' principle.

The most important step in the above method is hybridization with a special hybridization buffer, thereby allowing repeated subsequent hybridization and a sensitivity equivalent to or better than radioactive detection is obtained. Thus, the method according to the invention for the non-radioactive detection of nucleic acids containing e.g. 'single nucleotide polymorphisms' (SNP's) is to be regarded as a great improvement. In addition, the use of radioactivity which is hazardous to health may be avoided. Apart from that, by summarizing otherwise time-consuming intermediate steps and optimizing the compositions of solutions and the necessary washing parameters constant results may be achieved allowing to provide the basis for the future development of automated detection.

The test kit according to the present invention for the non-radioactive detection of nucleic acids containing e.g. 'single nucleotide polymorphisms' (SNPs) contains the following solutions:

Hybridization buffer: 5 l
500 ml 10×TNT
1250 ml of 20% SDS
10 g of blocking reagent (Boheringer Mannheim, DIG kit)
3250 ml of H₂O (twice distilled)
10×PBS: 5 l
516.2 g of Na₂HPO₄
132.6 g of NaH₂PO₄
198.7 g of NaCl
H₂O to 5 l pH: approx. 7.3
Buffer I: 5 l
10 g of blocking reagent
250 ml 10×PBS
125 ml of 20% SDS
4625 ml of H₂O (twice distilled), to be heated for 8 min. in a microwave oven, to be stirred until the blocking reagent is dissolved.
Buffer II: 5 l
250 ml 10×PBS
125 ml of 20% SDS
4625 ml of H₂O (twice distilled)
10×buffer III: 2 l
64.4 g of Tris HCl
1770 ml of H₂O (twice distilled)
210.4 g of diethanol amine pH: 9.75
Buffer IV: 5 l
4700 ml of H₂O (twice distilled)
50 ml of 0.5 M EDTA, pH 8.0
250 ml of 20% SDS
Buffer V: 1 1 l
920 ml of H₂O (twice distilled)
30 ml of 5 M NaCl
50 ml of 1 M TrisCl, pH 8.0
10×TNT: 1 l 44.4 g of Tris HCl
25.6 g of Tris base
73 g of NaCl
818 ml of H₂O ( )
100 ml of Triton X-100 pH: approx. 8.0

EXAMPLE

All steps are carried out at room temperature.

1. Membrane with the DNA side up in a dish with 180 ml hybridization buffer (28 mM Tris HCl/21 mM Tris base/125 mM NaCl/1% of Triton X-100/5% of SDS/0.2% of block reagent) to be prehybridized for 1 h.

2. Discard prehybridization solution. Centrifuge 5' biotinylated probe for 5 min. at max. speed and add it immediately in a final concentration of 10 pmol/ml to 100 ml of hybridization buffer (200 μM/5 μl). Hybridize membrane for 1 h.

3. Remove hybridization solution completely. Wash membrane 5× for 5 min. with 120 ml of buffer I (29 mM Na₂HPO₄/8 mM NaH₂PO₄/34 mM NaCl/0.5% of SDS, 0.2% of block reagent). Remove washing solution always completely. Make sure that big air bubbles will not be below the membrane.

4. Remove washing solution completely. Incubate membrane for 10 min. with 4 μl streptavidin alkaline phosphatase conjugate (alkaline phosphatase conjugate is obtained from Boehringer Ingelheim; centrifuge it for 5 min. at max. speed before adding it) in 100 ml buffer I.

5. Remove SvAP solution completely. Wash membrane 1× for 5 min. with 120 ml of buffer I and subsequently 6× for 5 min. with 120 ml of buffer II (29 mM Na₂HPO₄/8 mM NaH₂PO₄/34 mM NaCl/0.5% of SDS). Equilibrate subsequently the membrane 4× for 5 min. with 120 ml of buffer III (20 mM Tris HCl/100 mM diethanol amine/pH: 9.75).

6. In the mean time add 50 μl of CDPstar® (Tropix) to 10 ml of buffer III (1:200) and mix it thoroughly. Subsequently add the substrate solution into the middle of the 'CDPstar®only' dish.

7. Take membrane from the dish after completing the last equilibration step and drain it briefly. Subsequently the membrane will be placed onto the substrate solution with the DNA side down. By taking up and putting down the membrane repeatedly it is made sure that the substrate solution will be distributed uniformly below the membrane.

8. Drain the membrane briefly and fix it subsequently on a piece of plastic and cover it with transparent foil. Leave it for 30 min.

9. Put X-ray film on the covered membrane and expose it for 30 min. Carry out possibly shorter or longer (maximally for 2 h) exposures.

10. After exposing the film successfully put the membrane again into the dish and strip it with 120 ml of preheated buffer IV (5 mM EDTA/1% of SDS, 85° C.) 6× for 5 min.

11. Wash the membrane 1× with 120 ml of buffer V (50 mM Tris HCl/150 mM NaCl) and begin again with step 1. If the membrane is not to be immediately rehybridized it may be stored intermediately in buffer IV or between transparent foil.

What is claimed is:

1. A method for detecting membrane-bound nucleic acids comprising:

i) preincubating the membrane in a hybridization buffer consisting of 500 ml of 10×TNT, 1250 ml of 20% SDS, 10 g of blocking reagent and 3250 ml of H₂O;

ii) hybridizing the nucleic acids with a non-radioactively labeled probe in said hybridization buffer;

iii) washing at least twice in a buffer I consisting of 10 g of blocking reagent, 250 ml of 10×PBS, 125 ml of 20% SDS and 4625 ml of H₂O;

iv) incubating the membrane with a streptavidin alkaline phosphatase conjugate in buffer I;

v) washing the membrane once in buffer I, then washing at least twice in a buffer II consisting of 250 ml of 10×PBS, 125 ml of 20% SDS, 4625 ml of H₂O; then equilibrating the membrane in a buffer III consisting of 64.4 g of Tris HCl, 1770 ml of H₂O, 210.4 g of diethanol amine, pH 9.75;

vi) transferring the membrane to a solution of an alkaline phosphatase substrate in said buffer III; and vii) detecting a signal from a reaction of said alkaline phosphatase substrate with said alkaline phosphatase conjugate.

2. The method of claim 1, wherein the alkaline phosphatase substrate is (disodium 2-chloro-5-(4-methoxyspiro{1,2-dioxetane-3,2'-(5-chloro)-tricyclo[3.3.1.1$^{3,7}$]decan}-4-yl))-1-phenyl phosphate.

3. The method of claim 1, wherein all of steps i) to vii) are conducted at room temperature.

4. The method of claim 2, wherein all of steps i) to vii) are conducted at room temperature.

5. The method of claim 1, 2, 3, or 4 wherein the detecting step vii) is performed using X-ray film.

6. A kit comprising, in separate containers:

a hybridization buffer comprising 10×TNT, 20% SDS, and a blocking reagent;

10×PBS containing Na$_2$HPO$_4$, NaH$_2$PO$_4$, and NaCl, pH approximately 7.3;

a buffer I comprising a blocking reagent, 10×PBS and 20% SDS;

a buffer II comprising 10×PBS and 20% SDS;

10× buffer III comprising Tris-HCl and diethanol amine at pH 9.75, a buffer IV comprising EDTA and 20% SDS;

a buffer V comprising NaCl and Tris-Cl, pH 8.0; and

10×TNT comprising Tris-HCl, Tris-base, NaCl and Triton X-100, pH approximately 8.0.

7. A kit comprising, in separate containers:
a) a hybridization buffer consisting essentially of
   500 ml 10×TNT
   1250 ml of 20% SDS
   10 g of blocking reagent
   3250 ml of H$_2$O
b) 10×PBS consisting essentially of
   516.2 g of Na$_2$HPO$_4$
   132.6 g of NaH$_2$PO$_4$
   198.7 g of NaCl
   H$_2$O to make 5 l
a) buffer I consisting essentially of
   10 g of blocking reagent
   250 ml 10×PBS
   125 l of 20% SDS
   4625 ml of H$_2$O
d) buffer II consisting essentially of
   250 ml 10×PBS
   125 ml of 20% SDS
   4625 ml of H$_2$O
e) 10×buffer III consisting essentially of
   64.4 g of Tris HCl
   1770 ml of H$_2$O
   210.4 g of diethanol amine
f) buffer IV consisting essentially of
   4700 ml of H$_2$O
   50 ml of 0.5 M EDTA, pH 8.0
   250 ml of 20% SDS
g) buffer V consisting essentially of
   920 ml of H$_2$O
   30 ml of 5 M NaCl
   50 ml 1 M Tris Cl, pH 8
h) 10×TNT consisting essentially of
   44.4 g of Tris HCl
   25.6 g of Tris base
   73 g of NaCl
   818 ml of H$_2$O
   100 ml of Triton X-100.

\* \* \* \* \*